United States Patent
Parthasaradhi et al.

(10) Patent No.: US 7,491,726 B2
(45) Date of Patent: Feb. 17, 2009

(54) CRYSTALLINE FORMS OF ARIPIPRAZOLE

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Hyderabad, Andhrapradesh (IN)

( * ) Notice: Subject to any disclaimer, the term of this patent is extended or adjusted under 35 U.S.C. 154(b) by 590 days.

(21) Appl. No.: 10/508,498

(22) PCT Filed: Mar. 21, 2003

(86) PCT No.: PCT/IN03/00064

§ 371 (c)(1), (2), (4) Date: Sep. 21, 2004

(87) PCT Pub. No.: WO2004/083183

PCT Pub. Date: Sep. 30, 2004

(65) Prior Publication Data

US 2005/0159429 A1    Jul. 21, 2005

(51) Int. Cl.
*A61K 31/497*    (2006.01)
(52) U.S. Cl. ..................... 514/253; 544/363
(58) Field of Classification Search ................ 514/253; 544/363
See application file for complete search history.

(56) References Cited

U.S. PATENT DOCUMENTS 5,006,528 A    4/1991    Oshiro et al.
2004/0102523 A1    5/2004    Broquaire et al.

FOREIGN PATENT DOCUMENTS

EP    367 141 A1    5/1990

OTHER PUBLICATIONS

PCT International Search Report dated Mar. 21, 2003.
Journal of Medicinal Chemistry, vol. 41, No. 5, pp. 658-667 (1998).

*Primary Examiner*—James O. Wilson
*Assistant Examiner*—Ebenezer Sackey
(74) *Attorney, Agent, or Firm*—Caesar, Rivise, Bernstein, Cohen & Pokotilow, Ltd.

(57) ABSTRACT

The present invention provides novel crystalline forms of aripiprazole and aripiprazole hydrochloride, processes for their preparation and pharmaceutical compositions containing them.

6 Claims, 6 Drawing Sheets fig. 1 fig. 2 fig. 3 fig. 4 fig. 5 fig. 6

CRYSTALLINE FORMS OF ARIPIPRAZOLE

FIELD OF THE INVENTION

The present invention provides novel crystalline forms of aripiprazole and aripiprazole hydrochloride, processes for their preparation and pharmaceutical compositions containing them.

BACKGROUND OF THE INVENTION

Aripiprazole of formula (1):

or 7-[4-[4-(2,3-Dichlorophenyl)-1-piperazinyl]butoxy]-3,4-dihydro-2(1H)-quinolinone and its salts are useful for treating schizophrenia and their therapeutic uses were disclosed in U.S. Pat. No. 5,006,528.

Processes for the preparation of aripiprazole and its salts were described in U.S. Pat. No. 5,006,528. These processes do not produce well defined, reproducible crystalline forms.

Thus there is a need for stable and reproducible crystalline forms of aripiprazole and its salts.

We have discovered two novel crystalline forms of aripiprazole and four novel crystalline forms of aripiprazole hydrochloride. The novel forms have been found to be stable over the time and reproducible and so, suitable for pharmaceutical preparations.

Thus, the object of the present invention is to provide stable novel crystalline forms of aripiprazole, processes for preparation of the novel crystalline forms and pharmaceutical compositions containing these novel crystalline forms.

Another object of the present invention is to provide stable novel crystalline forms of aripiprazole hydrochloride, processes for preparation of the novel crystalline forms and pharmaceutical compositions containing these novel crystalline forms.

Since the novel crystalline forms of aripiprazole hydrochloride are obtained with high purity, preparation of aripiprazole via the crystalline forms of aripiprazole hydrochloride serves as a means of producing pure aripiprazole.

SUMMARY OF THE INVENTION

Figure 1:
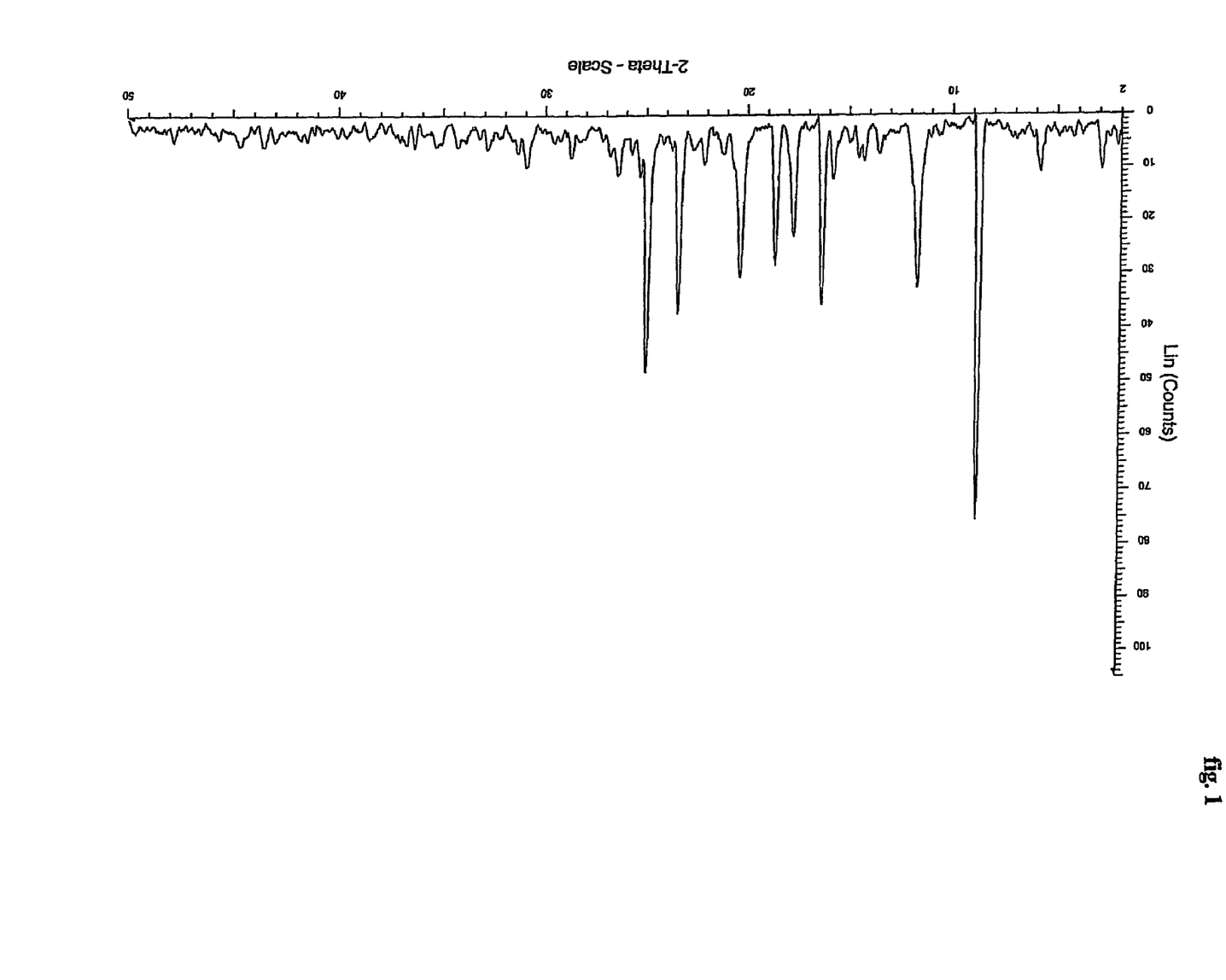
FIG. 1 is a x-ray powder diffraction pattern of crystalline Form I of aripiprazole.

According to one aspect of the present invention, there is provided a novel crystalline form of aripiprazole, designated as Form I, characterized by an x-ray powder diffraction pattern having peaks expressed as 2θ at about 8.7, 11.6, 16.3, 17.7, 18.6, 20.3, 23.4, 24.9 degrees. FIG. 1 shows typical Form I x-ray powder diffraction pattern.

According to another aspect of the present invention there is provided a process for preparation of the Form I of aripiprazole comprising the steps of:
a) dissolving aripiprazole in a suitable solvent;
b) refluxing for about 30 minutes to 1 hour;
c) cooling slowly to about 15° C. to 25° C.;
d) maintaining for about 2 hour to 4 hours at about 15° C. to 25° C.; and
e) filtering the solid separated.

The suitable solvent is selected from the group consisting of acetone, ethyl acetate, methanol or ethanol.

Figure 2:
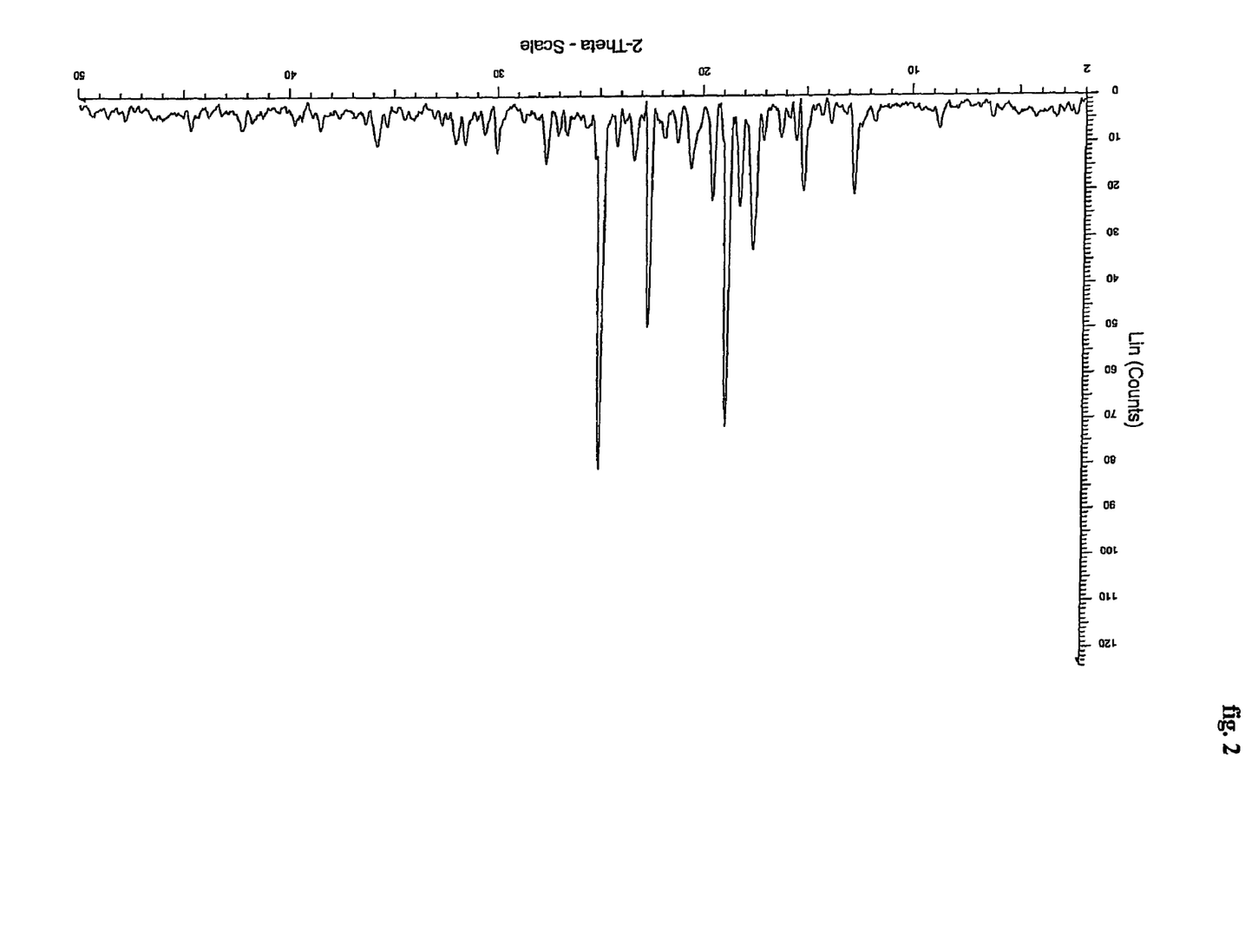
FIG. 2 is a x-ray powder diffraction pattern of crystalline Form II of aripiprazole.

According to another aspect of the present invention, there is provided a novel crystalline form of aripiprazole, designated as Form II, characterized by an x-ray powder diffraction pattern having peaks expressed as 2θ at about 12.7, 15.1, 17.5, 18.2, 18.8, 19.5, 20.6, 21.2, 22.6, 23.3, 24.2, 24.9, 27.6, 30.0, 31.6, 35.8 degrees. FIG. 2 shows typical Form II x-ray powder diffraction pattern.

According to another aspect of the present invention there is provided a process for preparation of the Form II of aripiprazole, which comprises dissolving aripiprazole in tetrahydrofuran and vacuum drying at about 25° C. or spray drying.

Figure 3:
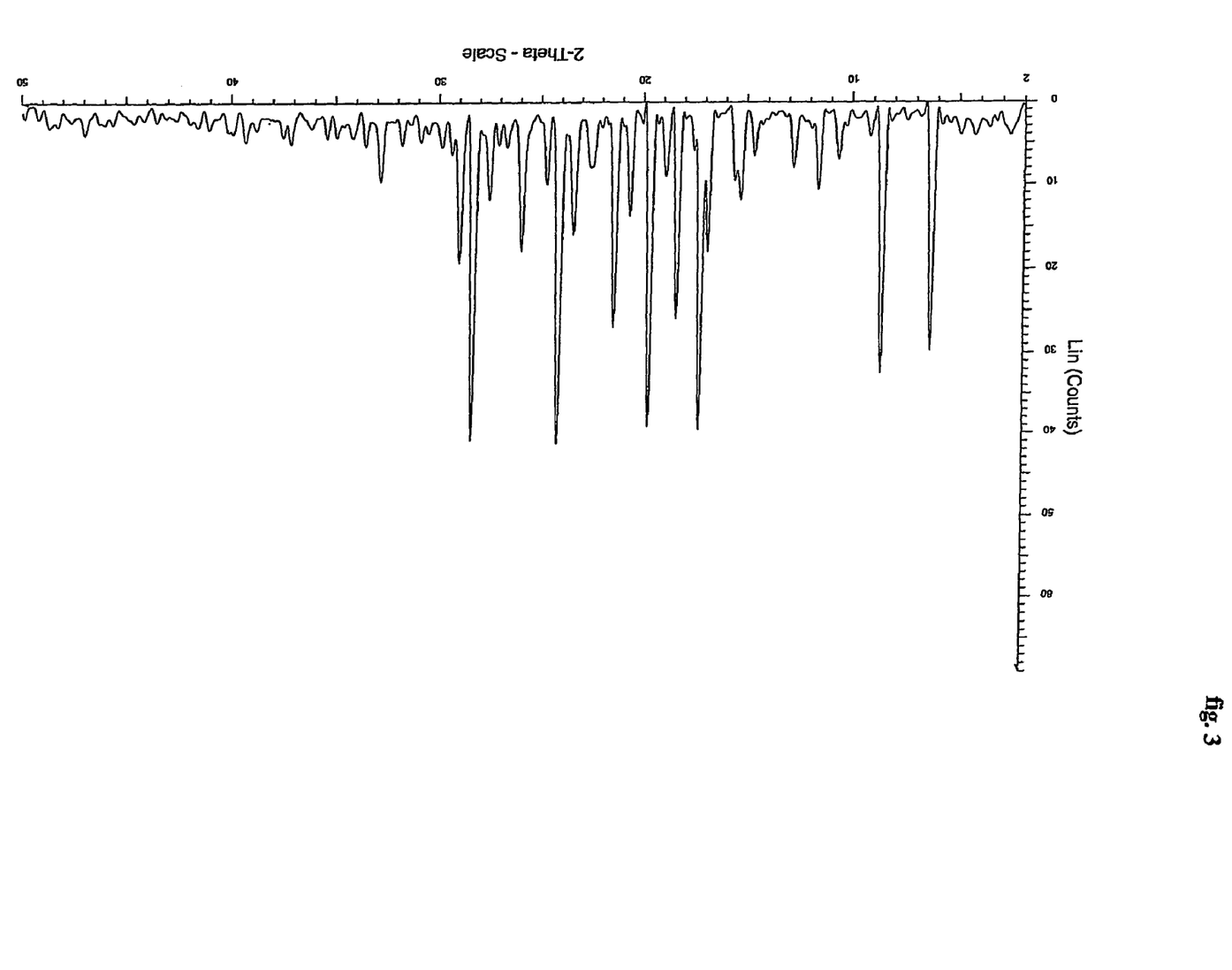
FIG. 3 is a x-ray powder diffraction pattern of crystalline Form A of aripiprazole hydrochloride.

According to another aspect of the present invention, there is provided a novel crystalline form of aripiprazole hydrochloride, designated as Form A, characterized by an x-ray powder diffraction pattern having peaks expressed as 2θ at about 6.2, 8.5, 11.5, 15.2, 15.5, 16.8, 17.2, 18.3, 18.9, 19.6, 20.6, 21.3, 23.4, 24.1, 24.7, 25.9, 27,5, 28.3, 28.9, 32.8 degrees. FIG. 3 shows typical Form A x-ray powder diffraction pattern.

According to another aspect of the present invention there is provided a process for preparation of the Form A of aripiprazole hydrochloride comprising the steps of:
a) dissolving aripiprazole in methanol or isopropyl alcohol;
b) adding hydrochloric acid;
c) maintaining for about 1 hour to 3 hours at about 15° C. to 25° C.;
d) filtering the solid separated.

Figure 4:
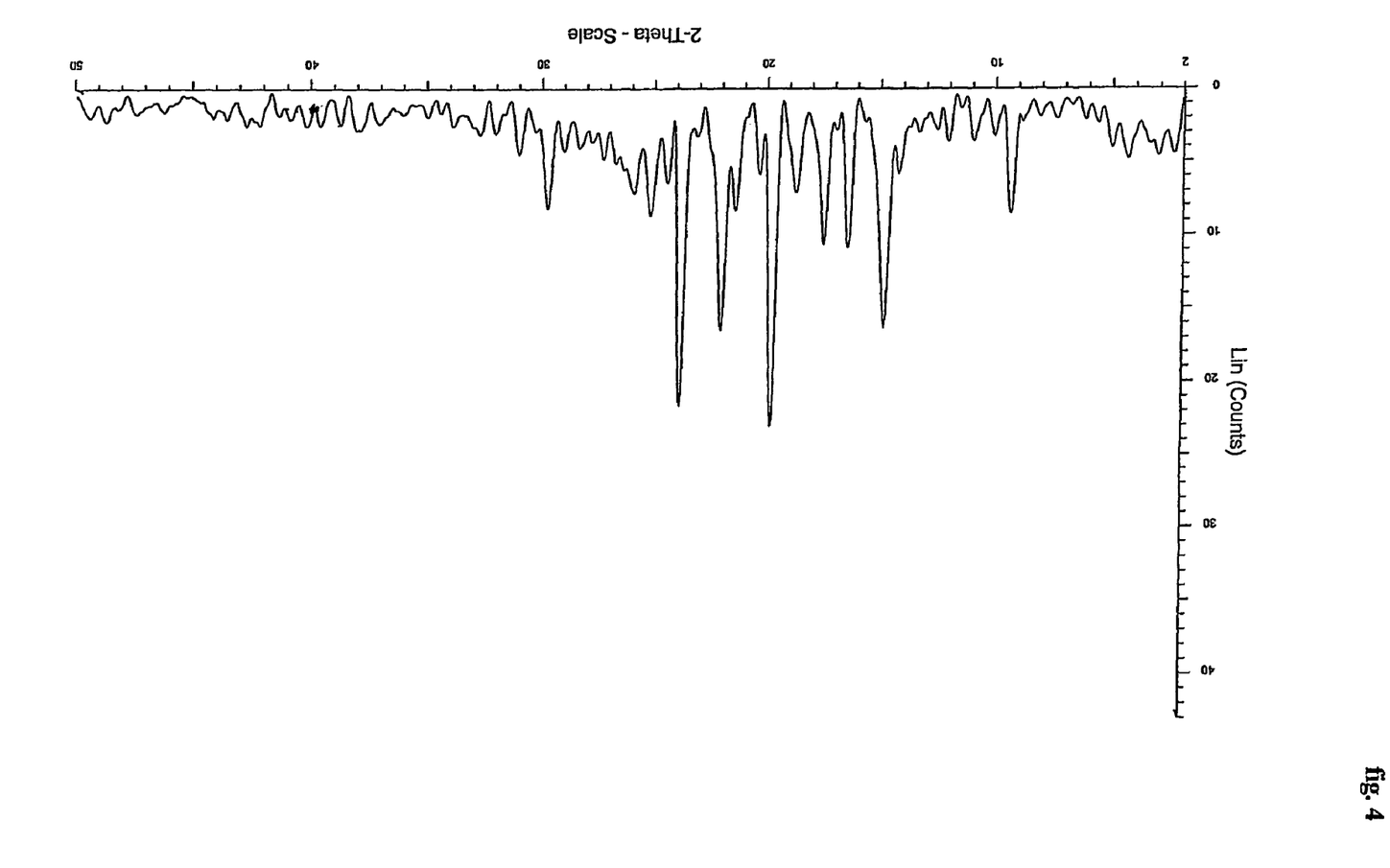
FIG. 4 is a x-ray powder diffraction pattern of crystalline Form B of aripiprazole hydrochloride.

According to another aspect of the present invention, there is provided a novel crystalline form of aripiprazole hydrochloride, designated as Form B, characterized by an x-ray powder diffraction pattern having peaks expressed as 2θ at about 9.3, 14.8, 16.4, 17.4, 18.7, 19.7, 21.4, 21.9, 23.8, 25.1, 25.9, 29.7 degrees. FIG. 4 shows typical Form B x-ray powder diffraction pattern.

According to another aspect of the present invention there is provided a process for preparation of the Form B of aripiprazole hydrochloride comprising the steps of:
a) dissolving aripiprazole in a ketonic solvent;
b) adding hydrochloric acid;
c) maintaining for about 1 hour to 4 hours at about 15° C. to 25° C.;
d) filtering the solid separated.

The ketonic solvent is selected from the group consisting of acetone, methyl isobutyl ketone and methyl ethyl ketone.

Figure 5:
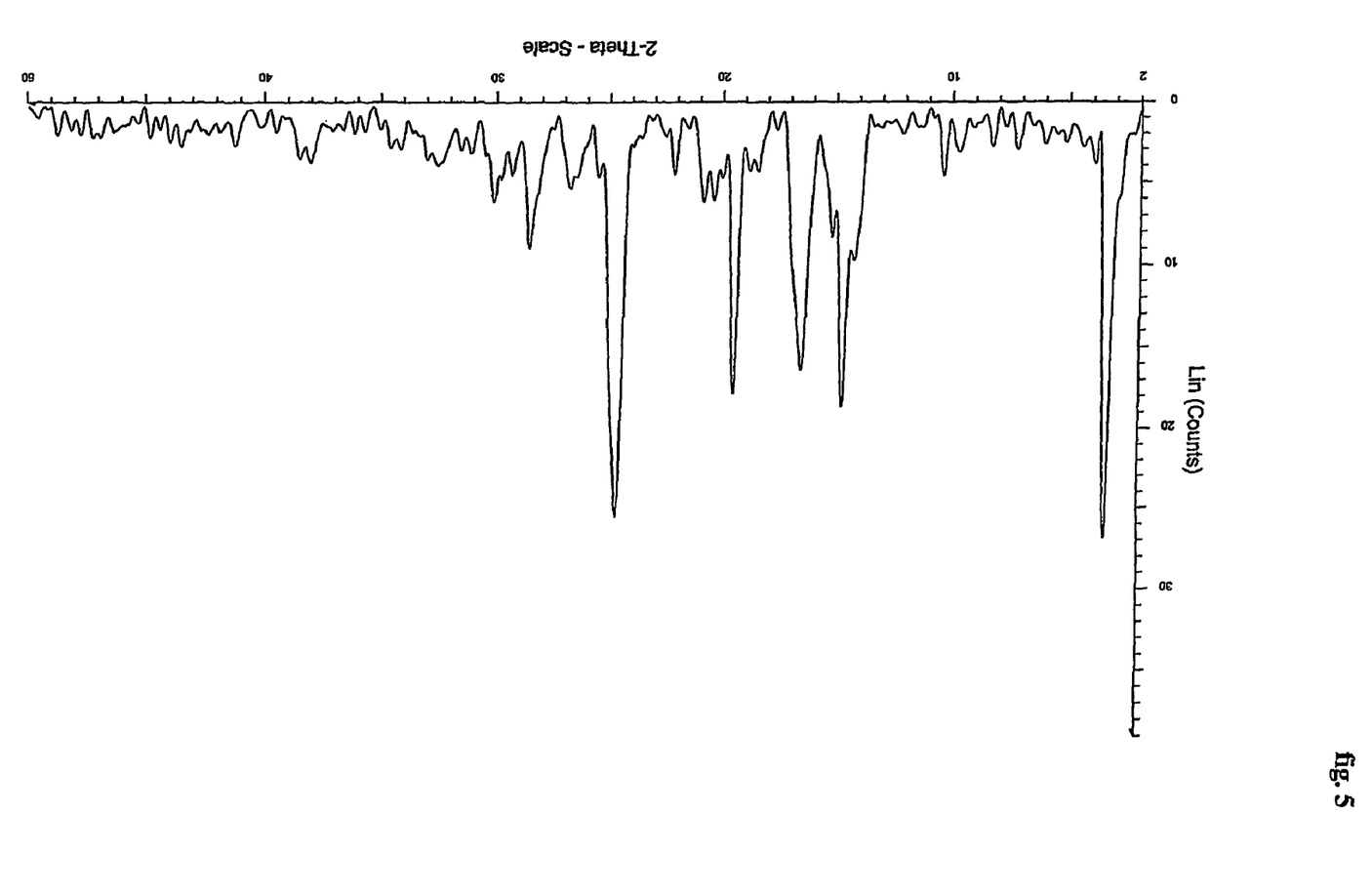
FIG. 5 is a x-ray powder diffraction pattern of crystalline Form C of aripiprazole hydrochloride.

According to another aspect of the present invention, there is provided a novel crystalline form of aripiprazole hydrochloride, designated as Form C, characterized by an x-ray powder diffraction pattern having peaks expressed as 2θ at about 3.3, 10.3, 14.2, 14.6, 15.1, 16.4, 16.6, 19.4, 20.3, 20.8, 24.5, 24.9, 25.5, 26.4, 26.7, 28.5, 29.3, 30.1 degrees. FIG. 5 shows typical Form C x-ray powder diffraction pattern.

According to another aspect of the present invention there is provided a process for preparation of the Form C of aripiprazole hydrochloride comprising the steps of:
a) dissolving aripiprazole in an ester solvent;
b) adding hydrochloric acid;
c) maintaining for about 1 hour to 4 hours at about 15° C. to 25° C.;
d) filtering the separated solid.

The ester solvent is selected from the group consisting of ethyl acetate, methyl acetate, ethyl formate and tert-butyl acetate.

Figure 6:
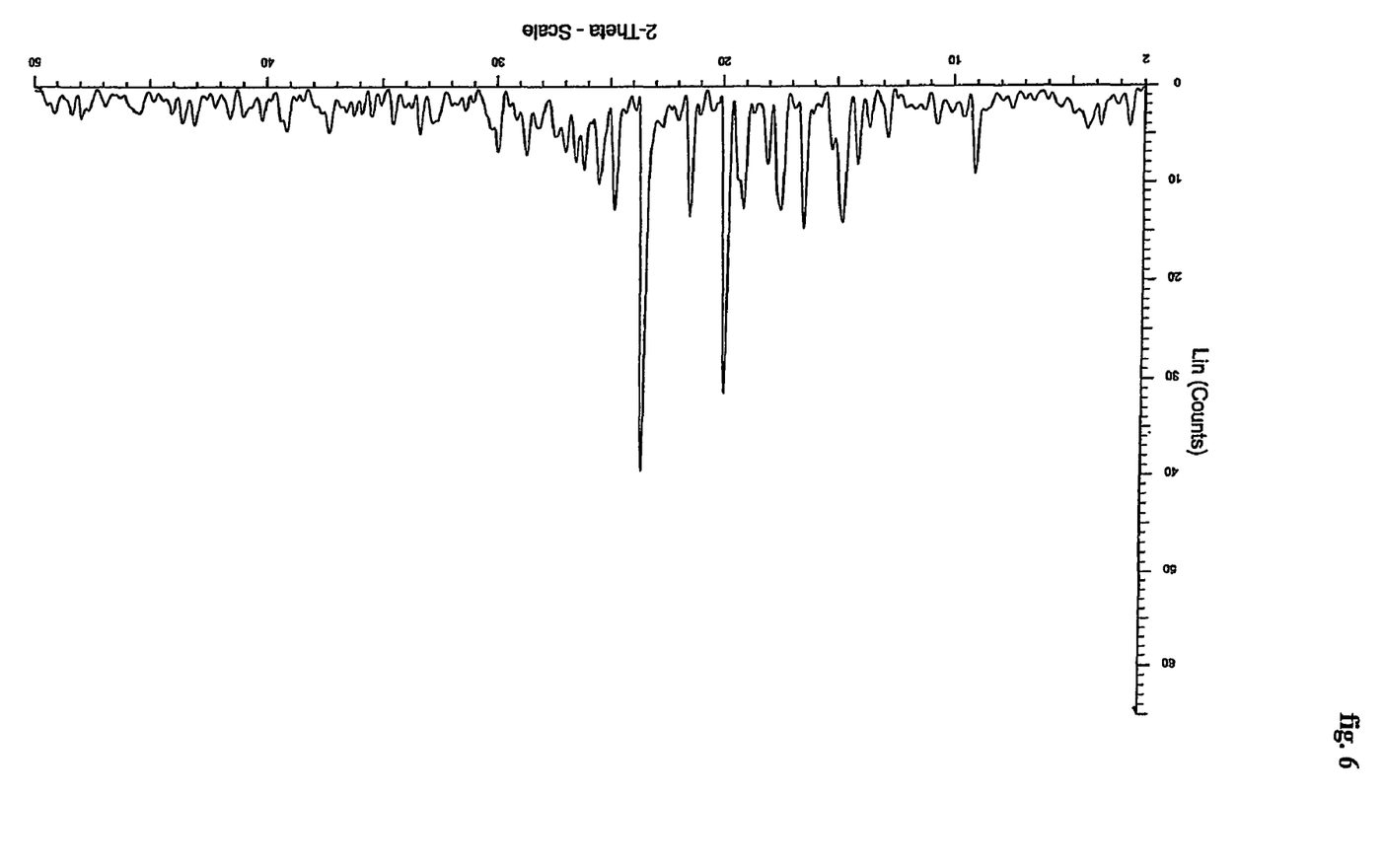
FIG. 6 is a x-ray powder diffraction pattern of crystalline Form D of aripiprazole hydrochloride.

According to another aspect of the present invention, there is provided a novel crystalline form of aripiprazole hydrochloride, designated as Form D, characterized by an x-ray powder diffraction pattern having peaks expressed as 2θ at about 9.0, 14.7, 16.4, 17.4, 19.0, 19.3, 19.8, 21.4, 23.4, 24.7, 25.4 degrees. FIG. 6 shows typical Form D x-ray powder diffraction pattern.

According to another aspect of the present invention there is provided a process for preparation of the Form D of aripiprazole hydrochloride comprising the steps of:
a) dissolving aripiprazole in tetrahydrofuran;
b) adding hydrochloric acid;
c) maintaining for about 2 hour to 4 hours at about 15° C. to 25° C.;
d) filtering the solid separated.

According to another aspect of the present invention there is provided a pharmaceutical composition comprising crystalline Form I or Form II of aripiprazole.

According to another aspect of the present invention there is provided a pharmaceutical composition comprising novel crystalline form of aripiprazole hydrochloride.

x-Ray powder diffraction spectrum was measured on a Siemens diffractometer.

DETAILED DESCRIPTION OF THE INVENTION

According to one aspect of the present invention, there is provided a novel crystalline form of aripiprazole, designated as Form I, characterized by an x-ray powder diffraction pattern having peaks expressed as 2θ at about 8.7, 11.6, 16.3, 17.7, 18.6, 20.3, 23.4, 24.9 degrees. FIG. 1 shows typical Form I x-ray powder diffraction pattern.

According to another aspect of the present invention, there is provided a process for preparation of the Form I of aripiprazole. Thus aripiprazole is dissolved in a suitable solvent. The suitable solvent is selected from the group consisting of acetone, ethyl acetate, methanol and ethanol. Aripiprazole obtained by a known method or crystalline Form II of aripiprazole obtained by the process described below may be used. The solution is refluxed for about 30 minutes to 1 hour. The solution is then cooled slowly to about 15° C. to 25° C. in about 1 hour and maintained for about 2 hour to 4 hours at the same temperature. The separated crystals are filtered and dried to give Form I of aripiprazole.

According to another aspect of the present invention, there is provided a novel crystalline form of aripiprazole, designated as Form II, characterized by an x-ray powder diffraction pattern having peaks expressed as 2θ at about 12.7, 15.1, 17.5, 18.2, 18.8, 19.5, 20.6, 21.2, 22.6, 23.3, 24.2, 24.9, 27.6, 30.0, 31.6, 35.8 degrees. FIG. 2 shows typical Form II x-ray powder diffraction pattern.

According to another aspect of the present invention there is provided a process for preparation of the Form II of aripiprazole, which comprises dissolving aripiprazole in tetrahydrofuran and vacuum drying at about 25° C. or spray drying.

According to another aspect of the present invention, there is provided a novel crystalline form of aripiprazole hydrochloride, designated as Form A, characterized by an x-ray powder diffraction pattern having peaks expressed as 2θ at about 6.2, 8.5, 11.5, 15.2, 15.5, 16.8, 17.2, 18.3, 18.9, 19.6, 20.6, 21.3, 23.4, 24.1, 24.7, 25.9, 27,5, 28.3, 28.9, 32.8 degrees. FIG. 3 shows typical Form A x-ray powder diffraction pattern.

According to another aspect of the present invention there is provided a process for preparation of the Form A of aripiprazole hydrochloride. Thus aripiprazole is dissolved in ethanol or isopropyl alcohol. If necessary, the solvent may be heated to effect dissolution of aripiprazole. Hydrochloric acid is added to the solution. Hydrochloric acid may be added as an aqueous solution or as a solution in any other solvent; or hydrochloric acid gas may be passed through the solution of aripiprazole. Then the contents are maintained for about 1 hour to 3 hours at about 15° C. to 25° C. and the separated crystals are filtered and dried to yield Form A of aripiprazole hydrochloride.

According to another aspect of the present invention, there is provided a novel crystalline form of aripiprazole hydrochloride, designated as Form B, characterized by an x-ray powder diffraction pattern having peaks expressed as 2θ at about 9.3, 14.8, 16.4, 17.4, 18.7, 19.7, 21.4, 21.9, 23.8, 25.1, 25.9, 29.7 degrees. FIG. 4 shows typical Form B x-ray powder diffraction pattern.

According to another aspect of the present invention there is provided a process for preparation of the Form B of aripiprazole hydrochloride. Thus aripiprazole is dissolved in a ketonic solvent. If necessary, the solvent may be heated to dissolve aripiprazole. The ketonic solvent is acetone or methyl isobutyl ketone or methyl ethyl ketone; or mixture thereof. Hydrochloric acid is added to the solution. Hydrochloric acid may be added as an aqueous solution or as a solution in any other solvent; or hydrochloric acid gas may be passed through the solution of aripiprazole. Then the contents are maintained for about 1 hour to 4 hours at about 15° C. to 25° C. and the separated crystals are filtered and dried to yield Form B of aripiprazole hydrochloride.

According to another aspect of the present invention, there is provided a novel crystalline form of aripiprazole hydrochloride, designated as Form C, characterized by an x-ray powder diffraction pattern having peaks expressed as 2θ at about 3.3, 10.3, 14.2, 14.6, 15.1, 16.4, 16.6, 19.4, 20.3, 20.6, 24.5, 24.9, 25.5, 26.4, 26.7, 28.5, 29.3, 30.1 degrees. FIG. 5 shows typical Form C x-ray powder diffraction pattern.

According to another aspect of the present invention there is provided a process for preparation of the Form C of aripiprazole hydrochloride. Thus aripiprazole is dissolved in an ester solvent. If necessary, the solvent may be heated to effect dissolution of aripiprazole. The ester solvent is selected from the group consisting of ethyl acetate, methyl acetate, ethyl formate and tert-butyl acetate. Hydrochloric acid is added to the solution. Hydrochloric acid may be added as an aqueous solution or as a solution in any other solvent; or hydrochloric acid gas may be passed through the solution of aripiprazole. Then the contents are maintained for about 1 hour to 4 hours at about 15° C. to 25° C. and the separated solid is filtered and dried to obtain Form C of aripiprazole hydrochloride.

According to another aspect of the present invention, there is provided a novel crystalline form of aripiprazole hydrochloride, designated as Form D, characterized by an x-ray powder diffraction pattern having peaks expressed as 2θ at about 9.0, 14.7, 16.4, 17.4, 19.0, 19.3, 19.8, 21.4, 23.4, 24.7, 25.4 degrees. FIG. 6 shows typical Form D x-ray powder diffraction pattern.

According to another aspect of the present invention there is provided a process for preparation of the Form D of aripiprazole hydrochloride. Thus aripiprazole is dissolved in tetrahydrofuran. Hydrochloric acid is added to the solution. Hydrochloric acid may be added as an aqueous solution or as a solution in any other solvent; or hydrochloric acid gas may be passed through the solution of aripiprazole. Then the contents are maintained for 2 hour to 4 hours at about 15° C. to 25° C. and the separated crystals are filtered and dried to produce Form D of aripiprazole hydrochloride.

The novel crystalline forms of aripiprazole hydrochloride obtained by the processes described above are very pure. So, aripiprazole with high purity can be obtained by basifying a solution of aripiprazole hydrochloride crystalline form and isolating aripiprazole from the solution by usual processes known in the art.

According to another aspect of the present invention there is provided a pharmaceutical composition comprising Form I or Form II of aripiprazole and a pharmaceutically acceptable carrier.

According to another aspect of the present invention there is provided a pharmaceutical composition comprising crystalline form of aripiprazole hydrochloride and a pharmaceutically acceptable carrier. The crystalline form may be Form A, Form B, Form C or Form D.

The forms of aripiprazole or aripiprazole hydrochloride may be formulated in a form suitable for oral administration or injection. The examples of pharmaceutical compositions are tablets, capsules, powders, suspensions, emulsions, injections and the like.

The following examples will serve to further illustrate the invention.

EXAMPLE 1

Aripiprazole (2 gm) (obtained by a process described in U.S. Pat. No. 5,006,528) is dissolved in acetone (42 ml) and refluxed for 30 minutes. The solution is slowly cooled to 25° C. in 1 hour and maintained at 25° C. for 3 hours. The separated crystals are filtered and dried to give 1 gm of Form I of aripiprazole.

EXAMPLE 2

Aripiprazole (2 gm) (obtained by a process described in U.S. Pat. No. 5,006,528) is dissolved in tetrahydrofuran and the solvent is removed by vacuum drying at 25° C. for 6 hours to give Form II of aripiprazole in quantitative yield.

EXAMPLE 3

Aripiprazole (2 gm) (obtained by a process described in U.S. Pat. No. 5,006,528) is dissolved in tetrahydrofuran and the solvent is removed by spray drying at 25° C. for 6 hours to give Form II of aripiprazole in quantitative yield.

EXAMPLE 4

Aripiprazole (2 gm) (obtained by a process described in U.S. Pat. No. 5,006,528) is dissolved in methanol (12 ml) and conc. hydrochloric acid (1 ml) is added to the solution. The contents are maintained for 2 hours at 25° C. and the separated solid is filtered to give 2 gm of Form A of aripiprazole hydrochloride.

EXAMPLE 5

Aripiprazole (2 gm) (obtained by a process described in U.S. Pat. No. 5,006,528) is dissolved in acetone (12 ml) and conc. hydrochloric acid (1 ml) is added to the solution. The contents are maintained for 3 hours at 25° C. and the separated solid is filtered to give 1.9 gm of Form B of aripiprazole hydrochloride.

EXAMPLE 6

Aripiprazole (2 gm) (obtained by a process described in U.S. Pat. No. 5,006,528) is dissolved in ethyl acetate (12 ml). 10% W/V HCl in ethyl acetate (4 ml) is added to the solution. The solution is maintained at 25° C. for 2 hours and the separated crystals are collected by filtration to give 2 gm of Form C of aripiprazole hydrochloride.

EXAMPLE 7

Aripiprazole (2 gm) (obtained by a process described in U.S. Pat. No. 5,006,528) is dissolved in tetrahydrofuran (12 ml) and conc. hydrochloric acid (1 ml) is added to the solution. The contents are maintained for 3 hours at 25° C. and the separated solid is collected by filtration to give 2 gm of Form D of aripiprazole hydrochloride.

EXAMPLE 8

Example 1 is repeated using Form II of aripiprazole instead of aripiprazole to give Form I of aripiprazole.

EXAMPLE 9

Example 2 is repeated using Form I of aripiprazole instead of aripiprazole to give Form II of aripiprazole.

EXAMPLE 10

Example 5 is repeated using Form I of aripiprazole instead of aripiprazole to give Form B of aripiprazole hydrochloride.

EXAMPLE 11

Example 7 is repeated using Form II of aripiprazole instead of aripiprazole to give Form D of aripiprazole hydrochloride.

We claim:

1. A crystalline Form I of aripiprazole characterized by an x-ray powder diffraction pattern having peaks expressed as 2θ at about 8.7, 11.6, 16.3, 17.7, 18.6, 20.3, 23.4, 24.9 degrees.

2. A crystalline aripiprazole of claim 1, characterized by an x-ray powder diffraction pattern as in FIG. 1.

3. A process for preparation of Form I of aripiprazole of claim 1, comprising the steps of:
   a) dissolving aripiprazole in a suitable solvent;
   b) refluxing for about 30 minutes to 1 hour;
   c) cooling slowly to about 15° C. to 25° C.;
   d) maintaining for about 2 hour to 4 hours at about 15° C. to 25° C.; and e) filtering the solid separated;

wherein the suitable solvent is selected from the group consisting of acetone, ethyl acetate, methanol and ethanol.

4. A process according to claim 3, wherein the suitable solvent is acetone.

5. A process according to claim 3, wherein the suitable solvent is ethyl acetate.

6. A pharmaceutical composition comprising the crystalline Form I of aripiprazole of claim 1 and a pharmaceutically acceptable carrier.

* * * * *